United States Patent [19]
Diamantstein et al.

[11] Patent Number: 5,631,349
[45] Date of Patent: May 20, 1997

[54] CHIMERIC MONOCLONAL ANTIBODIES RECOGNIZING HUMAN INTERLEUKIN-2-RECEPTOR

[75] Inventors: Tibor Diamantstein; Hisao Osawa, both of Berlin, Germany

[73] Assignee: Bayer Aktiengesellschaft, Leverkusen, Germany

[21] Appl. No.: 152,782

[22] Filed: Nov. 15, 1993

Related U.S. Application Data

[63] Continuation of Ser. No. 758,342, Sep. 9, 1991, abandoned, which is a continuation of Ser. No. 681,630, Apr. 2, 1991, abandoned, which is a continuation of Ser. No. 34,874, Apr. 6, 1987, abandoned.

[30] Foreign Application Priority Data

Apr. 14, 1986 [GB] United Kingdom .................. 8609058

[51] Int. Cl.$^6$ .................. C07K 16/28; C12N 5/20
[52] U.S. Cl. .................. 530/387.3; 530/388.22; 435/240.27
[58] Field of Search .................. 530/387.3, 388.22; 435/240.27, 172.2, 70.21; 424/85.8, 133.1, 143.1, 154.1

[56] References Cited

U.S. PATENT DOCUMENTS

| | | |
|---|---|---|
| 4,411,993 | 10/1983 | Gillis . |
| 4,578,335 | 3/1986 | Urdal . |
| 4,707,443 | 11/1987 | Nelson et al. . |
| 4,845,198 | 7/1989 | Urdal . |

FOREIGN PATENT DOCUMENTS

| | | |
|---|---|---|
| 0171496 | 2/1986 | European Pat. Off. . |
| 0226062 | 6/1987 | European Pat. Off. . |
| 0235805 | 9/1987 | European Pat. Off. . |
| 8601533 | 3/1986 | WIPO . |

OTHER PUBLICATIONS

Owasa et al., Immunology Letters 20: 205–212 1989.
Waldmann, Cancer Res. 45:45595–45615 1985.
Harris et al. Tibtech 11: 42–44, 1993.
Osband et al. Immunology Today 11:193–195, 1990.
Morrison, Science 229:1202–1207, 1985.
Herlyn et al. Cellular Immunology 92:105–114, 1985.
Shaw et al., J. Nat'l. Cancer Inst. 80: 1553–1559, 1988.
Shimuzu, et al. 1985 "Nucleotide sequence of . . . " Nucleic Acids Research 13(5):1505–1516.
Kirkman, et al. 1985 "Administration of . . . " J. Exp. Med. 162: 358–362.
Tanaka, et al., 1985 "Distinct Reactivities of Four Monoclonal Antibodies with . . . " Microbiol. Immunol. 29(10):959–972.
Tanaka, Microbiol Immunol. (1986) 30(4):373–388.
Molecular Immunology (1984), vol. 21, No. 12, pp. 1229–1236 Diamanstein et al.
Ey, P.L. et al., Immunochemistry (1978), vol. 15, pp. 429–436.
Lowry, O.H. et al., J. Biol. Chem. (1951), vol. 193, pp. 265–275.
Uchiyama, T. et al., J. Immunol. (1981), vol. 126, pp. 1398–1403.
Rubin, L.A. et al., Hybridoma (1985), vol. 4, pp. 91–102.
Kincade, P.W. et al., J. Immunol. Methods (1981), vol. 42, pp. 17–26.
Cantrell, D.A. et al., Science (Wash. DC) vol. 224, pp. 1312–1316.
Osawa H. et al., T. J. Immunol. (1984), vol. 132, pp. 2445–2450.
Reske-Kunz et al., J. Immunol. (1984), vol. 133, pp. 1356–1361.
Köhler et al., Nature, (1975), vol. 256, pp. 495–497.
Inhibition of IL 2–Dependent Proliferation of Rat T Lymphoblasts by the Monoclonal Antibody Art62 Which Reacts With MHC Class 1 Antigens[1] Hisaw Osawa vol. 134, No. 6, Jun. 1985 pp. 3901–3906 The Journal of Immunology.
A monoclonal Antibody which Recognizes the Human Receptor for T Cell Growth factor: Functional Effects and Use as a Probe to Investigate Receptor Regulation Joel M. Depper et al Lymphokines, vol. 9 pp. 128–152.
Immunological Reviews, No. 92, 1986, pp. 5–27, Munksgaard, Copenhagen, DK; T. Diamantstein et al.: "The interleukin-2 receptor, its physiology and a new approach to a selective immunosuppressive therapy by anti–interleukin–2 receptor monoclonal antibodies".
The Journal of Immunology, vol. 130, No. 1, Jan. 1983, pp. 51–55, The American Association of Immunologists; H. Osawa et al: "The characteristics of a monoclonal antibody that binds specifically to rat T lymphoblasts and inhibits IL 2 receptor functions".

*Primary Examiner*—Paula K. Hutzell
*Attorney, Agent, or Firm*—Sprung Horn Kramer & Woods

[57] ABSTRACT

Two chimeric monoclonal antibodies are disclosed which recognize the human interlukin-2-receptor and are capable of inhibiting interlukin-2 dependent lymphocyte proliferation. The antibodies comprise the variable regions of monoclonal antibodies AHT-54 or AHT-107 linked to a human Fc region.

2 Claims, 9 Drawing Sheets

ONE PARAMETER ANALYSIS

MEAN 21.26
SD 18.69
CV 87.90
LCV 0
RCV 512.03
HCV 55.65

FIG. 10

ONE PARAMETER ANALYSIS

MEAN 16.64
SD 13.18
CV 79.20
LCV 0
RCV 364.69
HCV 49.11

FIG. 11

ONE PARAMETER ANALYSIS

MEAN 16.99
SD 14.71
CV 86.60
LCV 20.50
RCV 284.75
HCV 75.43

CHIMERIC MONOCLONAL ANTIBODIES RECOGNIZING HUMAN INTERLEUKIN-2-RECEPTOR

This application is a continuation of application Ser. No. 07/758,342, filed Sep. 9, 1991, now abandoned which is a continuation of Ser. No. 07/681,630, filed Apr. 2, 1991 now abandoned; which is a continuation of Ser. No. 07/034,874, filed Apr. 6, 1987, now abandoned.

BACKGROUND OF THE INVENTION

1. Field of the Invention

This invention relates generally to new hybrid cell lines and more specifically to hybrid cell lines for production of monoclonal antibody to an antigen found on activated human lymphocytes, the interleukin-2-receptor, to the antibody so produced, and to therapeutic and diagnostic methods and compositions employing this antibody.

2. Background Information

For many, if not all cells, the initial trigger for proliferation appears to be the interaction of growth factors with the cell surface growth factor receptor. Activation of the growth factor receptor leads in turn to yet undefined cytoplasmic signalling systems.

Resting T lymphocytes are long living cells in the $G_o$ phase of the cell cycle. They only enter proliferative cycles under antigenic stimulation in the presence of a T cell growth factor, interleukin 2 (IL-2). Receptors for IL-2 are not detectable on the surface of resting T cells. Expression of IL-2 receptors (IL-2R) is the consequence of interaction of antigen with cells having the antigen receptor. As shown recently, IL-2 receptor expression is a transient event and repeated restimulation by lectins (Cantrell, P. A., and K. A. Smith, (1984), Science (Wash. D.C.) 224; 1312); (Osawa, H., and Diamantstein, T. (1984) J. Immunol.,132,2445) or the antigen (Reske-Kunz, A. B., D. v. Steldern, E. Rüde, H. Osawa and T. Diamantstein, (1984), J. Immunol.,133, 1356) is required for continuous IL-2 receptor expression and consequently for long term cell growth.

Since IL-2-R is expressed exclusively on activated lymphocytes, a monoclonal antibody (mAb) that reacts with the IL-2-R may be useful as a specific and selective immunosuppressive agent. Furthermore, such antibodies may serve as diagnostic reagents to detect qualitatively and quantitatively activated lymphocytes as well as neoplastic cells expressing IL-2-R.

SUMMARY OF THE INVENTION

An object of the present invention is to provide a composition of at least two monoclonal antibodies recognizing human interleukin-2-receptor and capable of inhibiting interleukin 2 induced lymphocyte proliferation. In a preferred embodiment, one or more of the antibodies are of the $IgG_1$ class. In another preferred embodiment the antibody composition is capable of inhibiting interleukin-2 binding to the receptor. The present invention provides monoclonal antibodies of the $IgG_1$ class recognizing human interleukin-2-receptor capable of inhibiting interleukin-2 binding to the receptor and in particular antibodies capable of inhibiting interleukin-2 dependent lymphocyte proliferation. The antibodies of the present invention can be used for preparation of chimeric animal-human antibodies recognizing human interleukin-2-receptor wherein the constant $F_c$ region of the immunoglobulin is obtained from human and the variable Fab region is obtained from an animal. Preferably the Fab region is obtained from mice.

The present invention further provides hybridoma cell lines, characterized by the production of monoclonal antibodies of the $IgG_1$ class recognizing human interleukin-2-receptor. Particular preferred are the hybridoma cell lines having the NTCC designation numbers ECACC 86 04 1801 and ECACC 86 04 1802. The hybridomas producing monoclonal antibodies AHT-54 and AHT-107 were deposited with PHLS, CAMR, Porton Down, Salisbury, Wilts England on Apr. 18, 1986 under accession numbers ECACC 86041801 and 86041802, respectively.

Human T-lymphoblasts expressing IL-2-R were prepared by known methods (Osawa, H., and Diamantstein, T.,(1983), J. Immunol., 130,51.) and were used to produce a mouse monoclonal antibody against IL-2-R by the technique of Kohler and Milstein (Köhler, G., and C. Milstein, (1975) Nature, 256,495). The fusion resulted in two hybrid clones AHT-54 and AHT-107 producing anti-IL-2-R antibodies of $IgG_1$ subclass. The hybrid clones secreting anti-IL-2-R antibodies were selected as preferred embodiments of the present invention.

Both mAb i) inhibit binding of $^{125}I$ labelled IL-2 to IL-2-R positive human lymphocytes, ii) inhibit IL-2 dependent proliferation in vitro and iii) precipitate the identical cell surface molecule of 55 KD, the IL-2 binding protein. Competitive binding of AHT-54 and AHT-107 revealed that they recognize different eptiopes of the IL-2-R molecule.

ART-107 is different from anti-Tac (Uchiyama, T. et al., (1981) J. Immunol.,126,1398) i) because competitive inhibition studies revealed that they recognize two different epitopes of the IL-2-R molecule; AHT-107 is also different from 7G7 B6, a recently published anti-human IL-2-R mAb (A. Rubin, C. Kurman, E. Biddison, D. Goldman, and L. Nelson,(1985), Hybridoma,Vol. 4,91), because in contrast to 7G7 B6, AHT-107 inhibits binding of IL-2 to the IL-2-R as well as IL-2 dependent proliferation of lymphocytes.

Both monoclonal antibodies (mAb) react specifically with activated lymphocyte (T and B), but not with resting lymphocytes or other non-lymphoid cells. This statement is based on FACS-analysis data(see FIGS. 6–11).

According to previous studies in animal model such antibody (Ab) reacting with the rat (ART-18) and with the mouse IL-2-R (AMT-13 and M7/20) has been shown to inhibit selectively and specifically i) local GVH-reaction (Diamantstein, T. and H. Osawa, (1986), Immune Rev., 92 in press.) ii) cardiac allograft rejection (L. Kirkman, E. Kelley, A. Koltun, J. Schoen, A. Ythier and B. Strom, (1985), Transplantation, 40,719.), (L. Kirkman, L. V. Barrett, N. Gaulton, E. Kelley, A. Ythier and B. Strom, (1985), J. Exp. Med.,162, 358.) and iii) T-cell-mediated autoimmune reaction such as acute autoimmune encephalomyelitis and adjuvant arthritis induced by T-cell transfer (Wekerle, H. and T. Diamantstein, (1986), Autoimmunity: Experimental and Clinical Aspects, Eds: R. S. Schwarz, N. R. Rose. Ann. New York Acad. Sci., In press.)

The anti-IL-2-R monoclonal antibodies of the present invention are also useful as therapeutic agents in clinical syndromes which are associated with pathological proliferation of IL-2 dependent cells. Thus, for example, hyperimmune syndromes such as Host versus Graft (HvG), Graft versus Host (GvH) diseases and autoimmune diseases (e.g. multiples sclerosis, autoimmune diabetis, Crohn's disease) may be treated. In a preferred embodiment of the present invention, the anti-IL-2-R monoclonal antibodies are used as therapeutic agents directly without further modification thereof. Furthermore, the invention includes preparation of anti IL-2-R chimeric antibodies using the human heavy chain of different classes and subclasses in combination with the variable region of the AHT-54 and AHT-107 mAb, in order to optimize the therapeutic use.

Thus, the present invention also concerns a chimeric animal-human antibody recognizing human interleukin-2-receptor. In such chimeric antibody, the $F_c$ region can be obtained from a human and the Fab region can be obtained from an animal, e.g., a mouse.

Alternatively, the antibodies may be coupled to drugs including cytotoxic agents. The monoclonal antibodies of the present invention are capable of recognizing specifically cells expressing IL-2 receptors, inhibiting their function and of eliminating them selectively.

The monoclonal antibodies of the present invention are also useful diagnostic reagents for cells which contain IL-2-R either on the cell surface or within the cells and in body fluids. Thus by means of the present invention, cells containing IL-2-R may be identified in samples having different kinds of cells. Localization of IL--2-R containing cells is possible in cultured cell colonies or in tissue specimens. When used in this manner the monoclonal antibodies are preferably coupled to fluorescent, color-forming substances such as an enzyme (ELISA) or chromophor, or a radioactive substance (RIA).

Such antibodies are useful in a method of treating syndromes associated with pathological proliferation of IL-2 dependent cells comprising administering a therapeutically effective amount AHT-54 and AHT-107 thereof.

DETAILED DESCRIPTION OF THE INVENTION

The following description is intended to illustrate this invention without limiting the same in any manner especially with respect to substantially functional equivalents of hybridomas and monoclonal antibodies as described herein.

I. Production of mAb

Source of IL-2-R

IL-2-R expressing cells were prepared as described using human-T-lymphoblast. Mixed human peripheral blood lymphocytes were stimulated with 3 mg/ml of concanavalin A (Con A) for 3 days. The cells were converted, treated with α-methyl mannoside (20 mg per ml), washed and used as immunogens in culture medium. Cultures were maintained in Click's RPMI medium (Seromed GmbH, München, Federal Republic of Germany) supplemented with $2\times10^{-3}$M L-glutamine, $5\times10^{-5}$M 2-mercaptoethanol, 100 U ml$^{-1}$ penicillin, 100 µg ml$^{-1}$ streptomycin, and 5 to 10% (v/v) fetal calf serum (FCS; batch No. 104; Seromed GmbH).

Immunization, cell fusion, cloning, and production of monoclonal antibodies (mAb)

Ten-week-old BALB/c mice were primed with $2\times10^7$ T lymphoblasts. The cells were injected in 0.1 ml portions ($10^6$ cells) subcutaneously into the footpads and into the necks of the mice as well as i.v. ($10^7$ cells in 0.5 ml). Four weeks later, the mice were challenged i.v. with $10^7$ T-lymphoblasts. Three days later, spleen cells from the immunized mice were fused with X63-Ag8.653 mouse myeloma cells in the presence of polyethylene glycol (Köhler and Milstein, (1975), Nature,256,495, as modified by Lemke H., G. J. Hämmerling, C. Höhmann and K. Rajewsky, (1978), Nature 271,249). Fused cells suspended in HAT medium were distributed into each well of ten 24-well tissue culture plates (1 to $2\times10^6$ spleen cells/well). Supernatants of the wells in which vigorous growth was observed after 3 to 4 weeks were screened for their capacity to bind a) human T lymphoblasts, b) mouse T lymphoblasts, and c) human thymocytes attached to the surface of the wells of microtiter plates. Cell-bound immunoglobulin was then detected by enzyme-linked immunosorbent assay (ELISA) as described (Kincade, P. W., G. Lee, L. Sun, and T. Watanabe, (1981), J. Immunol. Methods,42,17.) by using β-galactosidase-coupled sheep F(ab')$_2$ anti-mouse immunoglobulin (New England Nuclear, Dreieich, Federal Republic of Germany) as a second antibody. The hybridomas grown in HAT or RPMI medium that constantly produced antibodies binding specifically to human T lymphoblasts were selected. Supernatants of growing hybridomas were repeatedly tested and selected for hybridomas producing supernatants active in the functional assay (inhibition of the T-lymphoblast response to IL-2) as well as the absorption assay (inhibition of the capacity of T lymphoblasts to absorb IL 2 after preincubation). Positive hybridomas were cloned by limiting dilution with mouse thymocytes used as a feeder layer. The clones were retested and expanded. The supernatants of the relevant clones were used for isolation and purification of the mAb.

Purification of the mAb

As tested in the Ouchterlony double immunodiffusion test with rabbit anti-mouse IgM, IgA, IgG1, IgG2a, IgG2b, and IgG$_3$ sera (Miles Laboratories, Ltd., Slough, England), the hybridoma clonesAHT-54 and AHT-107 were found to produce IgG1 antibodies. Excepting the initial screening experiments, in which unpurified culture supernatants were used, the following experiments were performed with purified IgG1. Purification was achieved by successive binding/ elution from protein A-Sepharose (Pharmacia Fine Chemicals) according to the method described by Ey et al, (Ey, P. L., S. J. Prowse and C. R. Jenkin, (1978), *Immunochemistry*, 15,429). About 600 ml of the culture supernatants, brought to pH 8.0, were passed over a 5 ml protein A-Sepharose column equilibrated in 0.1M sodium phosphate buffer (pH 8.0). IgG1 was eluted from the column with 0.1M sodium citrate buffer (pH 6.0). The purified antibody was then dialyzed against a buffer containing 0.01M HEPES (pH 7.4) and 0.9% NaCl. The purity of mAb was confirmed by sodium dodecyl sulfate (SDS) polyacrylamide gel electrophoresis performed in reducing conditions as described (Laemmli, U. K. 1970. Cleavage of structural proteins during the assembly of the head of bacteriophage $T_4$. *Nature*, 227, 429). The protein concentration of the purified IgG1 was determined by absorption of ultaviolet light at 280 nm, assuming an extinction coefficient (1% w/v:1 cm) of 14, and by the method of Lowry et al, 1951 (Lowry, O. H., N. J. Rosebrogh, A. L. Farr, and R. J. Randall,(1951), *J. Biol. Chem.*, 193, 265.) with bovine serum albumin (BSA) used as the standard.

Recombinant Interleukin-2 provided from Sanolez Mend was used. $^{125}$I-labelled recombinant IL-2 was produced from NEN.

Labelling of the mAB with $^{125}$I

MoAb were labelled with $^{125}$I according to McConahey and Dixon (McConahey, P. J., and F. J. Dixon, (1980), *Methods Enzymol*, 70:210). Briefly, 20 µg of IgG1 dissolved in 60 µl of Na$^{125}$J (100 mCi ml$^{-1}$, carrier-free; Amersham Buchler). Ten microliters of chloramine-T (2.5 mg ml$^{-1}$ in 0.05M Na—P) were added to the mixture. After 45 seconds of incubation at room temperature, 20 µl of $Na_2S_5O_5$ (3 mg ml$^{-1}$ in 0.05 Na—P) were added to the tube. The mixture was immediately loaded onto a 15-ml Sephadex G-75 column (prewashed with 0.05M Na—P containing 4% BSA and washed consecutively with 0.05M Na—P until the eluate was protein-free), and the radiolabel in the excluded fraction was collected.

DETAILED DESCRIPTION OF THE DRAWINGS

Figure 1A:
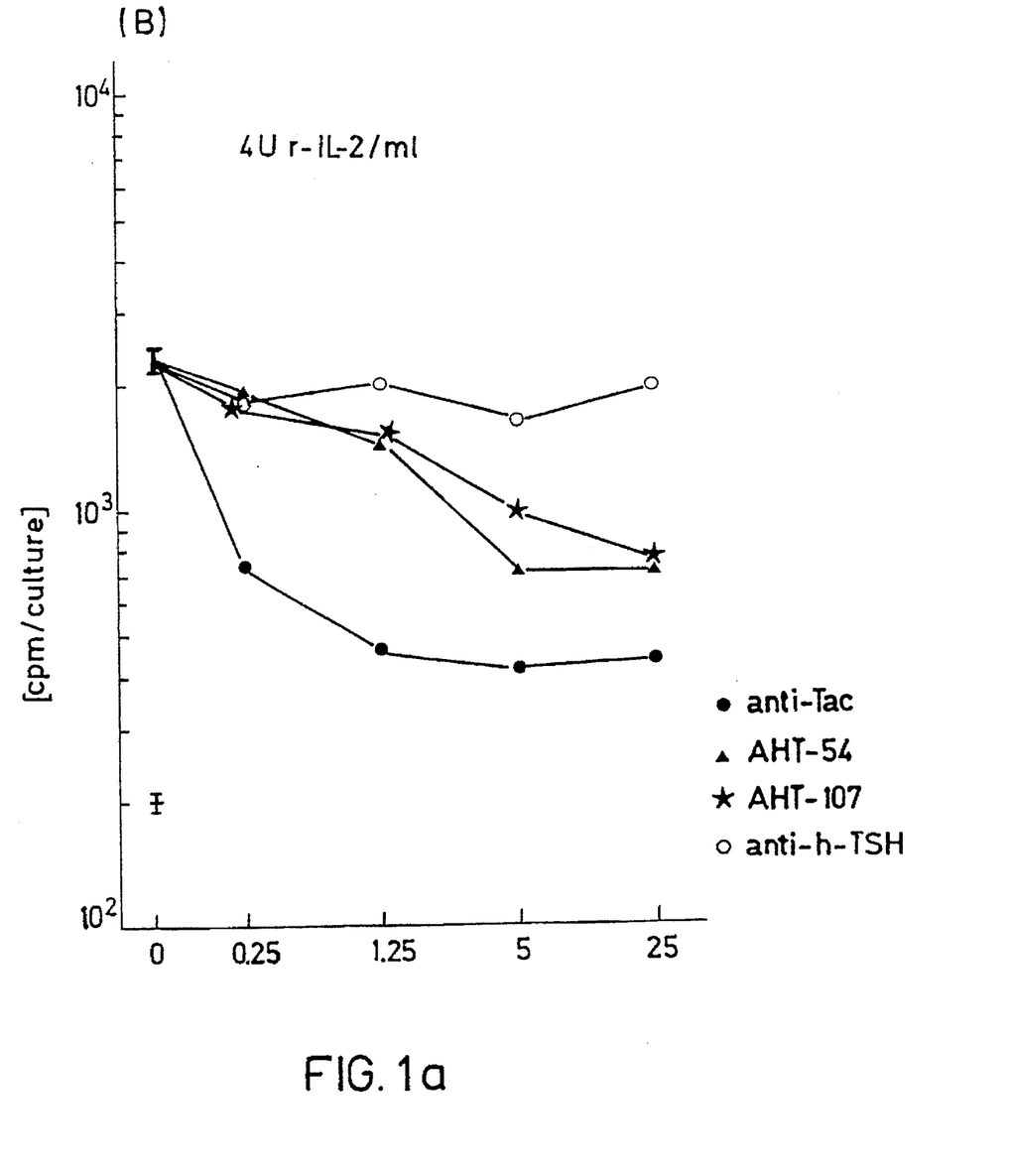
FIG. 1a is a graph of $^3$H-TdR uptake [cpm/culture] vs. m Ab[Mg/ml] for four different monoclonal antibodies for 4 U/ml of recombinant IL-2.
Figure 1B:
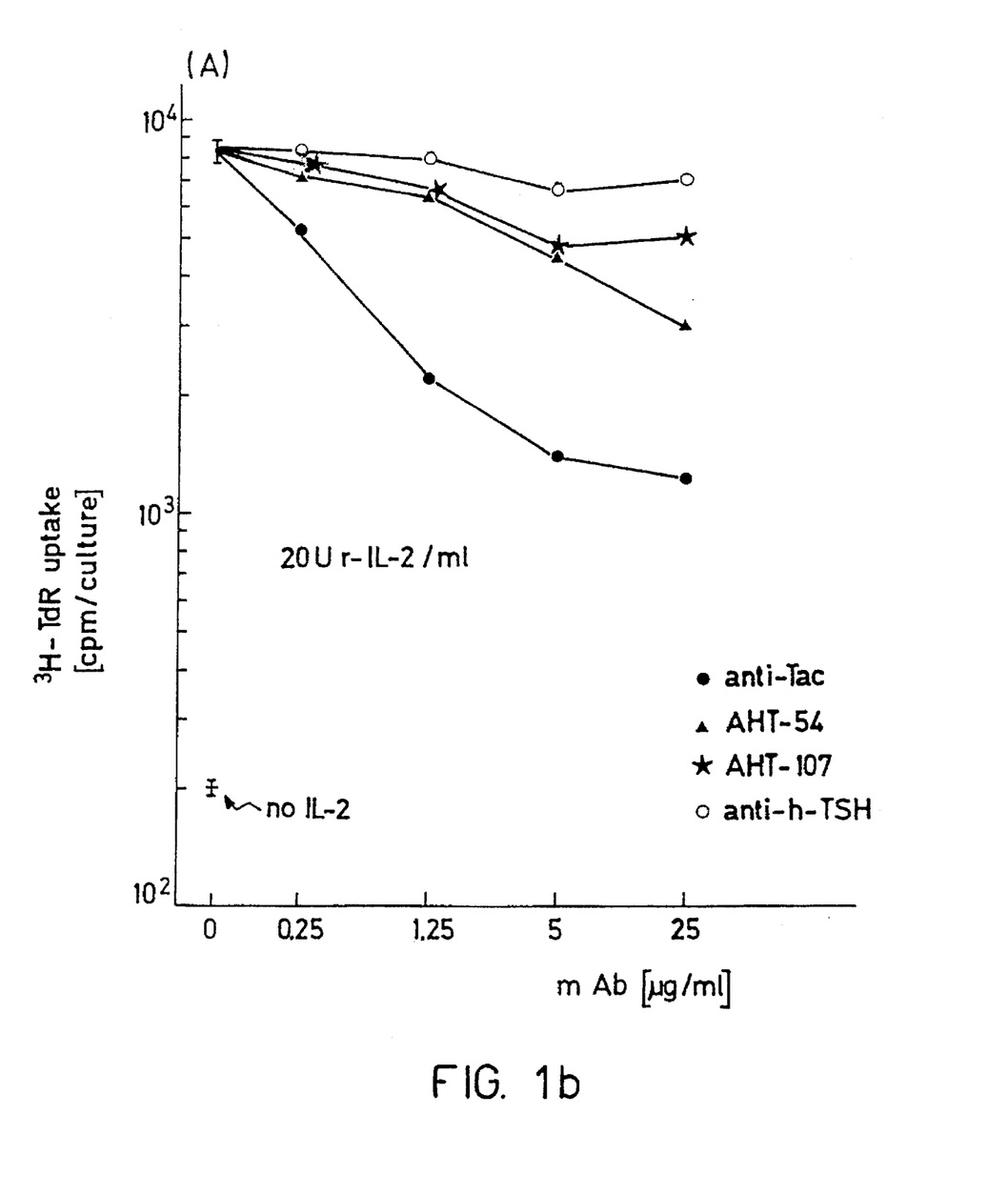
FIG. 1b is a graph of $^3$H-TdR uptake vs. mAb for four different monoclonal antibodies for 20 U/ml of recombinant IL-2.

FIG. 1

Inhibition of IL-2 dependent human T-lymphoblast proliferation by different mAbs $2 \times 10^6$ human T-lymphoblasts were incubated for 3 days in 0.2 ml of medium containing the indicated amounts of recombinant IL-2 (FIG. 1a, 4 u/ml; FIG. 1b, 20 u/ml) in the absence or presence of the different mAbs, anti-Tac (-o-), AHT-54 (-Δ-), AHT-107 (-*-) and of a control mAb anti-human-TSH (-o-). The cells were pulsed with $^3$H-thymidine for the last 4 hours of the incubated period. Incorporation of $^3$H-thymidine was measured according to the standard procedure (Diamantstein et al, *Mol. Immunol.*, (1984), 21,1229.

Figure 2:
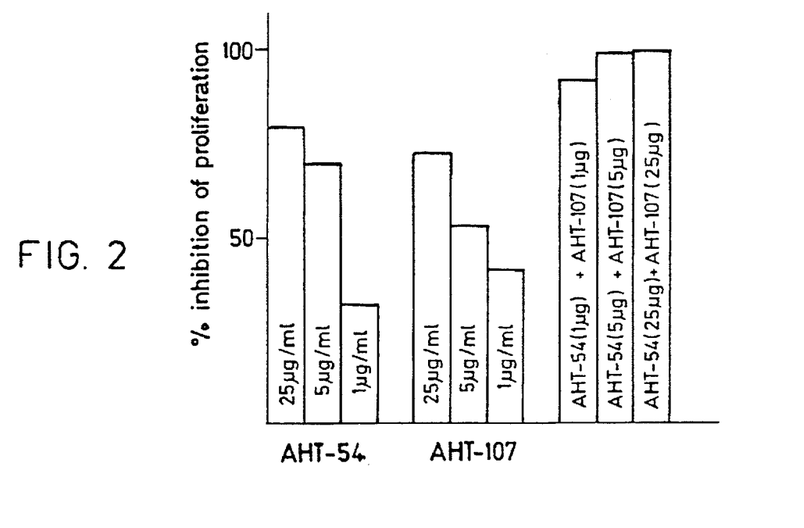
FIG. 2 consists of three sets of bar graphs (three per set) showing % inhibition of proliferation for AHT-54 in AB, AHT-107 in AB and combinations thereof.

FIG. 2

Synergistic action of AHT-54 and AHT-107 mAbs on IL-2 dependent proliferation

T-lymphoblasts were cultured with 4 u/ml of r-IL-2 for 3 days (for detail see FIG. 1) in the presence of either AHT-54 or AHT-107 mAB or in combination of both mAbs.

Figure 3A:
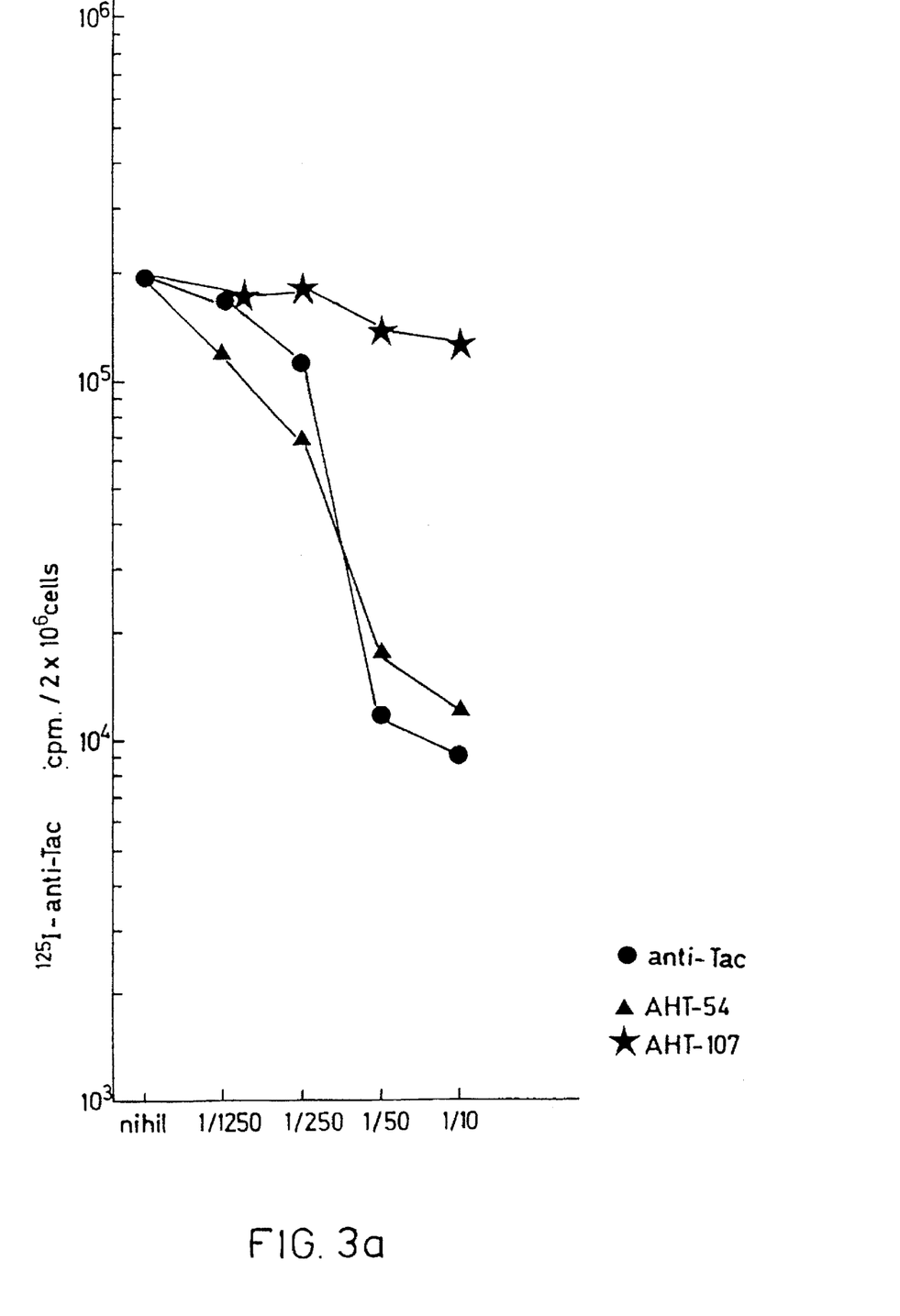
FIG. 3a is a plot of $^{125}$I-anti-Tac binding (cpm/2×10$^6$ cells) in the presence of various dilutions of anti-Tac, AHT-54 and AHT-107.
Figure 3B:
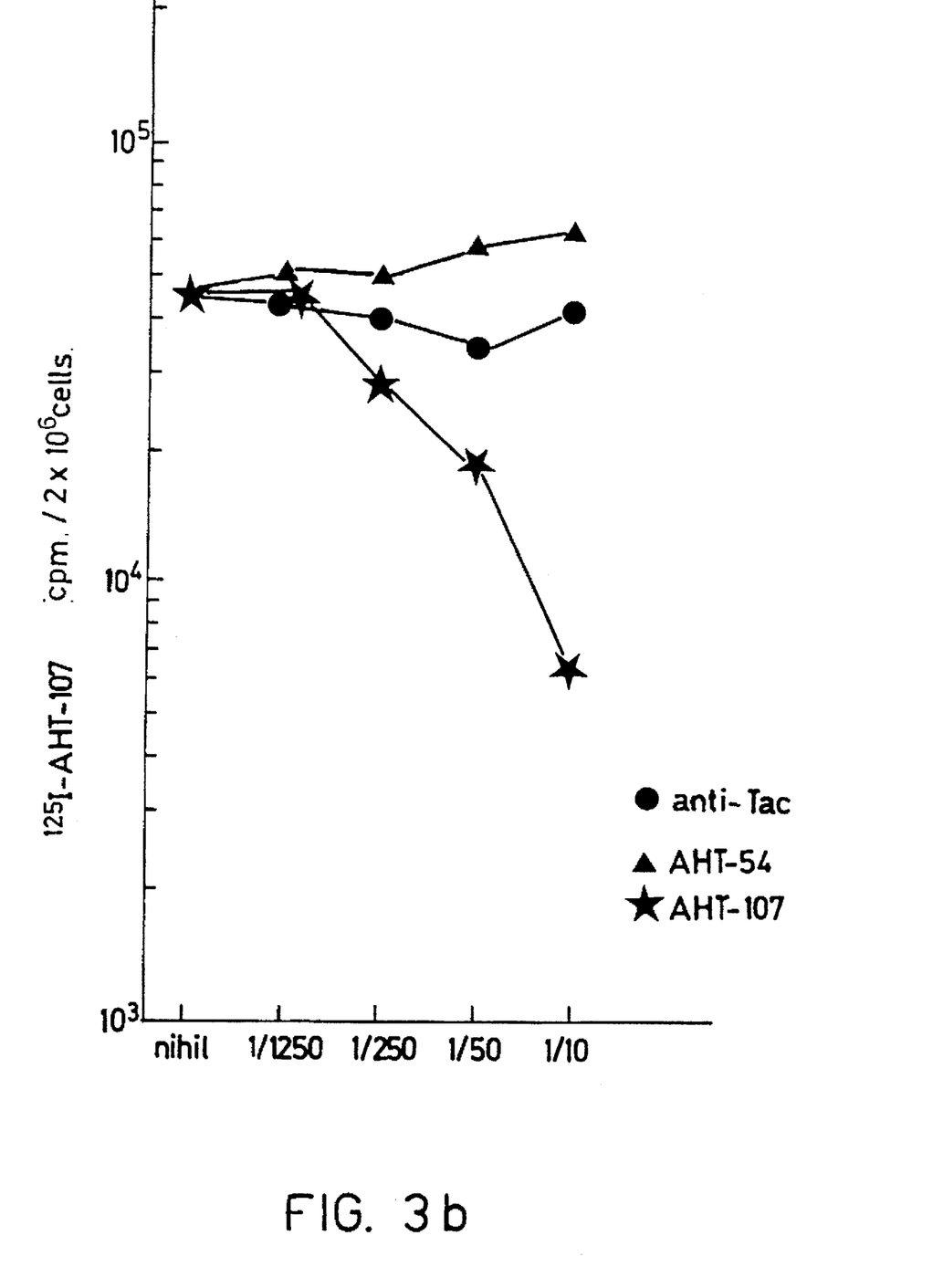
FIG. 3b is a plot of $^{125}$I-AHT-107 binding (cpm/2×10$^6$ cells) in the presence of various dilutions of anti-Tac, AHT-54 and AHT-107.
Figure 3C:
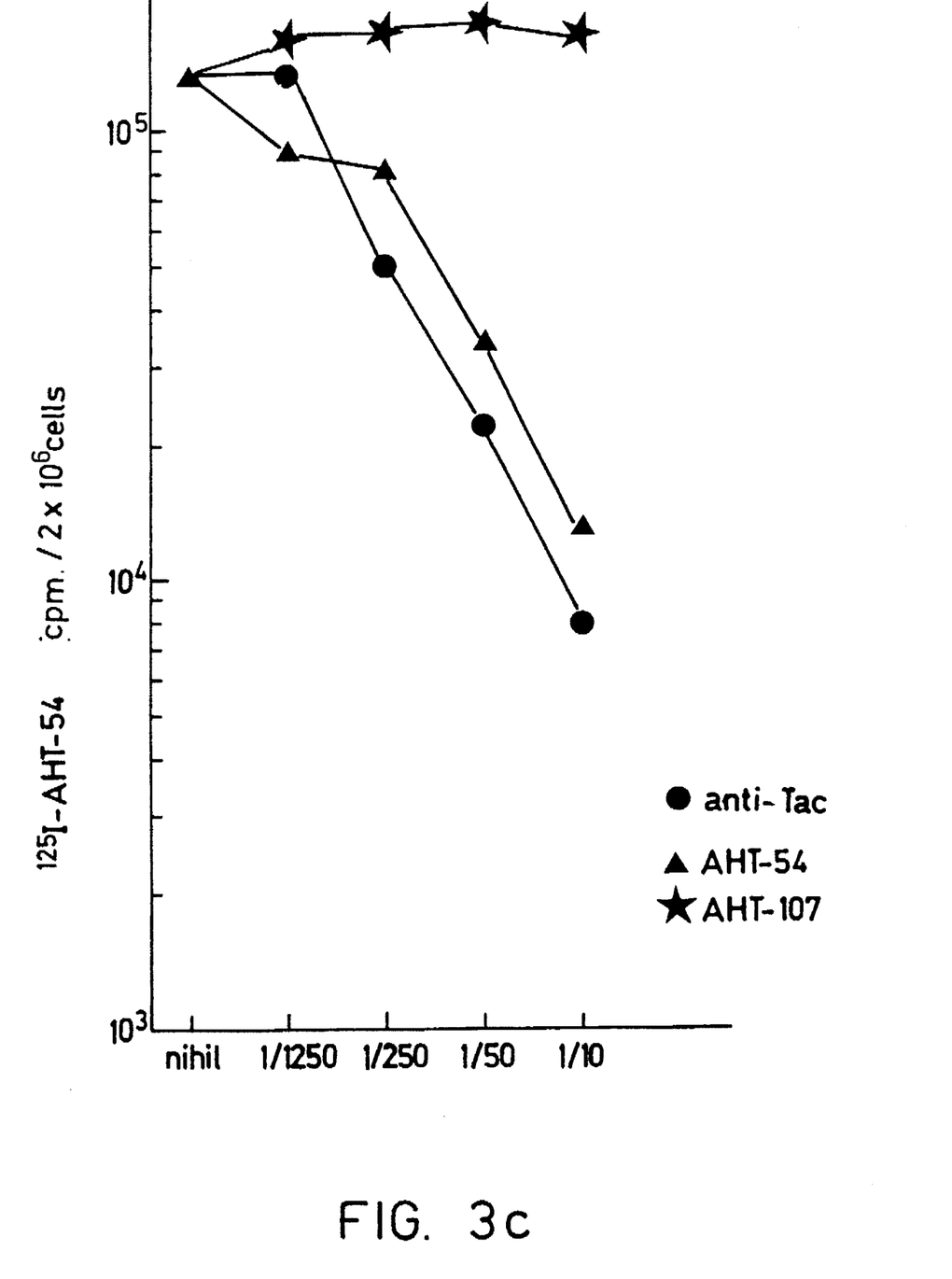
FIG. 3c is a plot of $^{125}$I-AHT-54 binding (cpm/2×10$^6$ cells) in the presence of various dilutions of anti-Tac, AHT-54 and AHT-107.

FIG. 3

Competition for the binding of $^{125}$I-labelled antibodies $2 \times 10^6$ human T blasts were first suspended in 100 µl of a binding buffer (PBS=0.5% BSA;10 mM NaN$_3$) containing different dilutions of one of the mAbs:anti-Tac (-o-), AHT-54 (-Δ-) and AHT-107 (-*-). Each suspension was mixed with 100 µl of a 1:40 dilution of one of the $^{125}$I-labelled mAbs.

Each mixture was incubated for 1 hour at 4° C. The relative amount of $^{125}$I-labelled mAb (cpm) bound to the pelleted cells was measured by using a gamma-radiation counter after washing them twice with the binding buffer.

Figure 4:
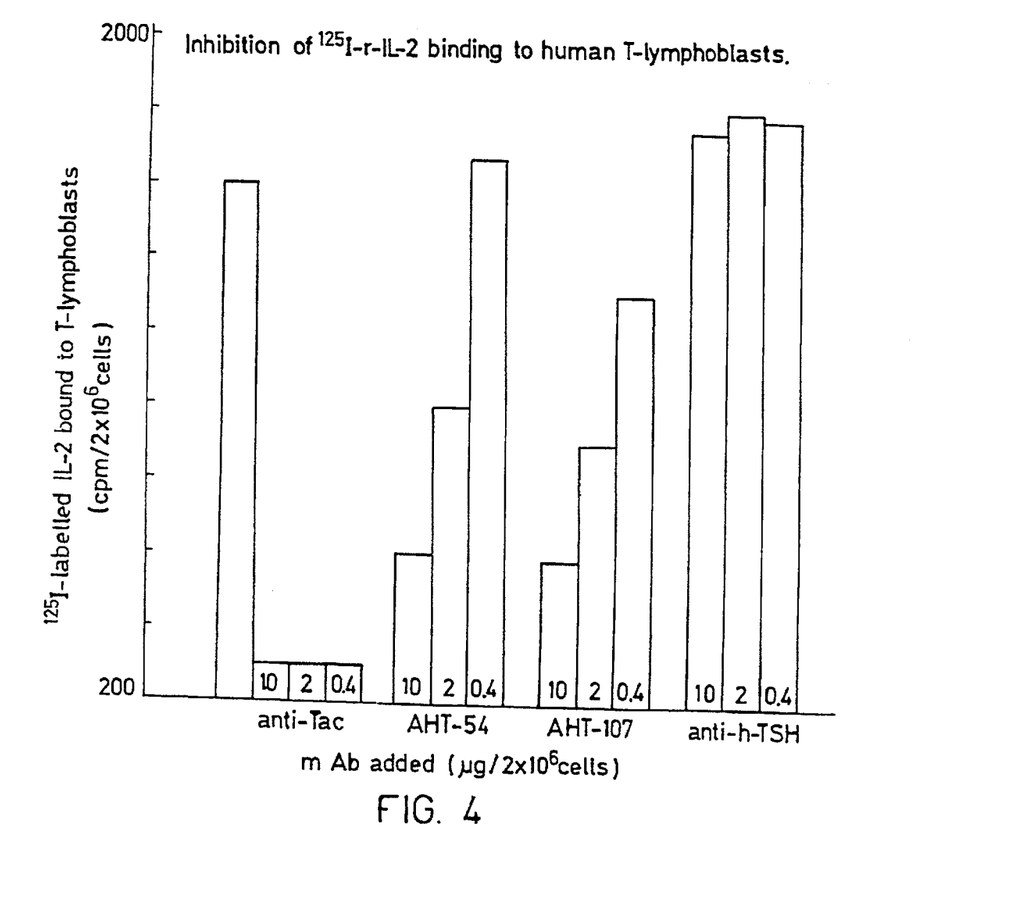
FIG. 4 is a series of bar graphs of $^{125}$I-labelled 1L-2 bound to T-lymphoblasts (cpm/2×10$^6$ cells) vs. mAb added (µg/2× 10$^6$ cells) for anti-Tac, AHT-54, AHT-107 and anti-h-TSH.

FIG. 4

Inhibition of $^{125}$I-IL-2 binding to human T blasts by different mAbs $2 \times 10^6$ human T blasts were first incubated for 30 min. at 37° C. in 0.25 ml of a buffer (RPMI/Hepes/BSA/NaN$_3$) containing the indicated amounts of different mAbs. The incubation was further continued at 37° C. in the presence of $^{125}$I-IL-2. After 40 minutes the incubation mixture was centrifuged to pellet the cells and the pelleted cells were taken up in 100 µl of the buffer and overlaid on the oil phase consisting of dibutylphthalate/olive oil (10+3). After centrifugation the tips of the tube containing the cell pellets were cut out and counted in a gamma-radiation counter.

Figure 5:
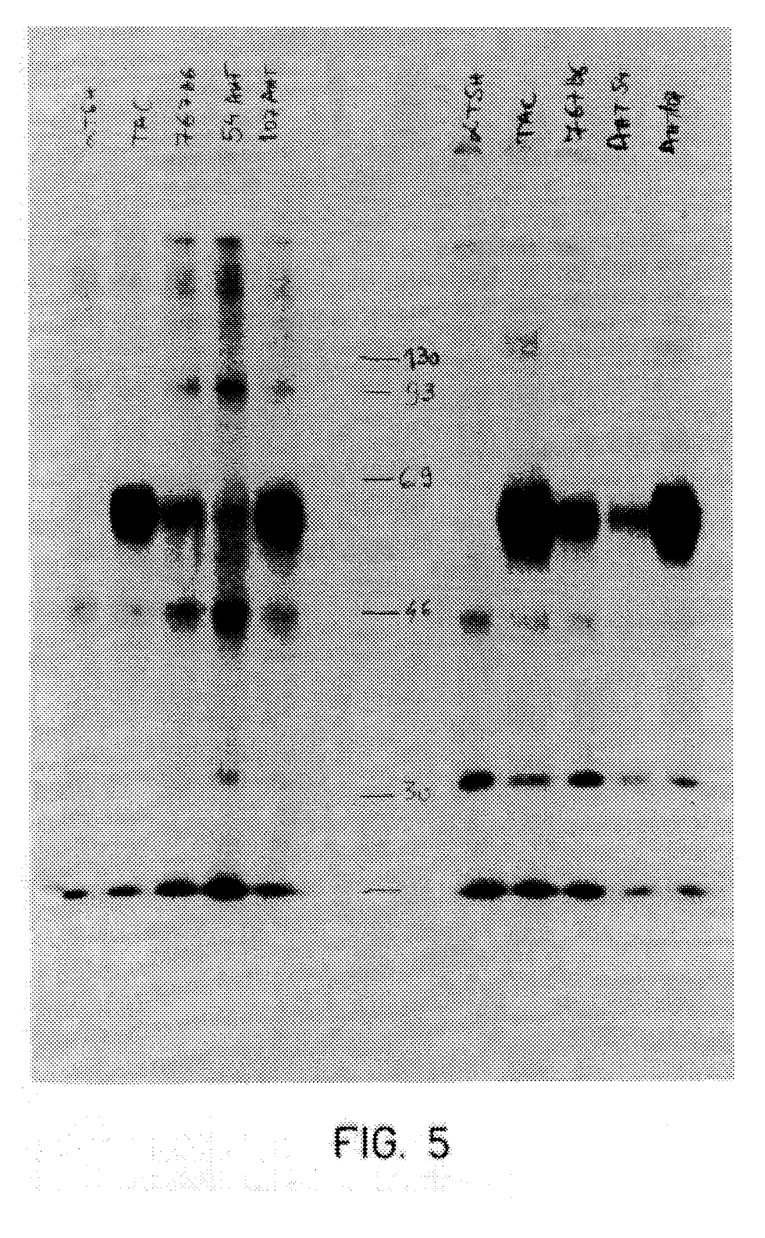
FIG. 5 is a SDS-PAGE analysis of immunoprecipitation under non-reducing conditions (lanes 1–6) or reducing conditions (lanes 7–12) for various mAbs.

FIG. 5

SDS-PAGE analysis of immunoprecipitates with different mAbs $2 \times 10^7$ human T blasts were surface-iodinated with 0.5 mCi of Na [$^{125}$I] and lysed in 0.5 ml of the lysis buffer. The lysate was centrifuged and preabsorbed with ⅕ volume of protein A-sepharose beads (10 µl) through a bridge antibody rabbit anti-mouse IgG. After 1 hour at 4° C. the beads were washed three times with a buffer containing 50 mM Tris-HCL, pH 8.3, 450 mM NaCl, 5 mM KI, 0.02% NaN$_3$ and 0.5 Nonidet P-40, and extracted with 100 µl of the sample buffer. 50 µl aliquots of the extracts were subjected to SDS-PAGE analysis either under non-reducing (lanes 1–6) or reducing (lanes 7–12) conditions. The mAbs used were control mouse UPC-10 ascites (lanes 1 & 7), anti Tac ascites (lanes 2 & 8), AHT-54 ascites lanes 4 & 10), AHT-107 ascites (lanes 5 & 11) and AHT-107 culture supernatants (lanes 6 & 12).

FIGS. 6 to 11

FACS-analysis

Human peripheral blood cells (HPBL) and activated T-lymphoblasts derived from HPL were incubated at 4° C. in presence of 0.1% NaN$_3$ for 30 minutes with AHT-54 or ART-107 mAB (1:1000 ascites fluid and as negative control with a TSH, washed and stained using saturating amount of goat anti-mouse IgG labelled with FITC). Fluorescence activated cell sorter analysis performed with Epics V.

Figure 6:
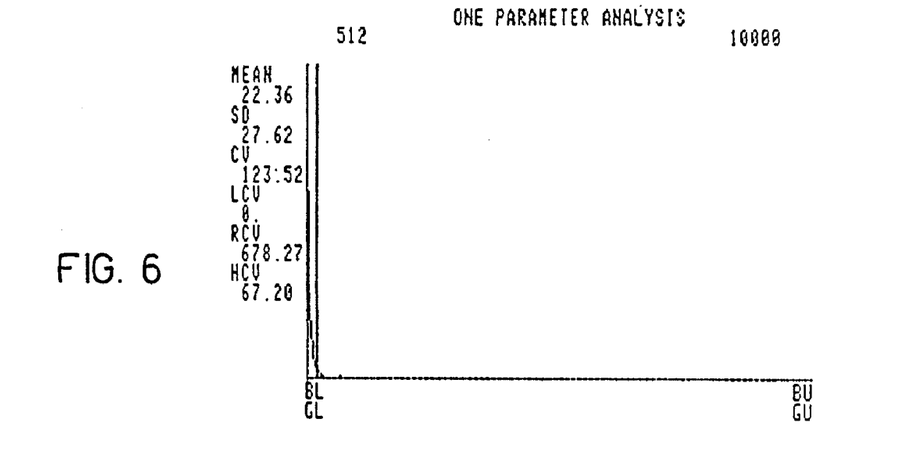
FIG. 6 shows the results of fluorescence activated cell sorter (FACS) analysis for a negative control and T-lymphoblasts.
Figure 7:
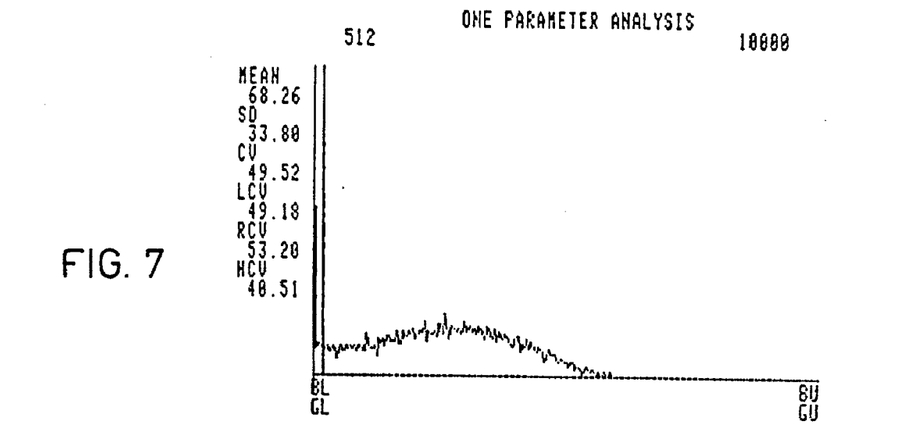
FIG. 7 shows a FACS analaysis for AHT-54 and T-lymphoblasts.
Figure 8:
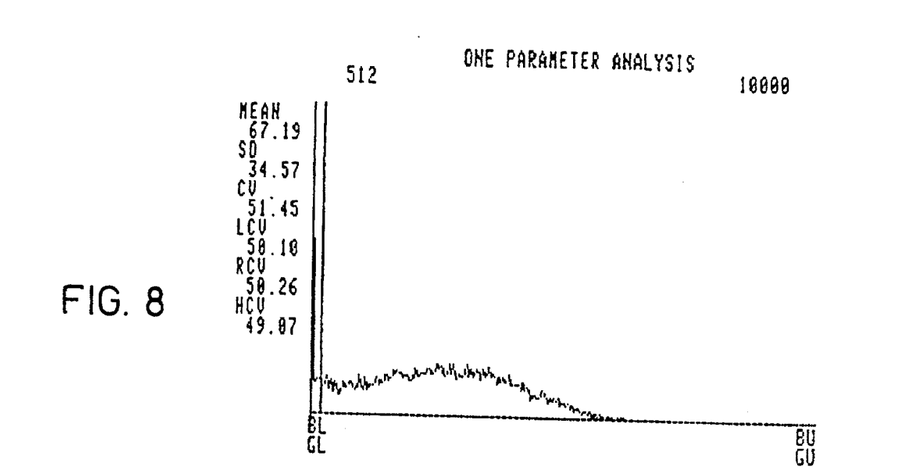
FIG. 8 shows a FAC analysis for AHT-107 and T-lymphoblasts.
Figure 9:
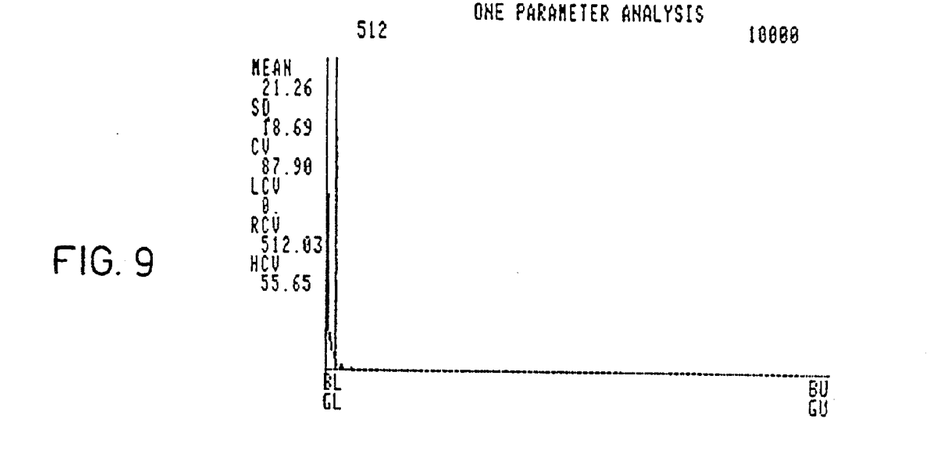
FIG. 9 shows a FACS analysis for a negative control and human peripheral blood cells (HPBL).
Figure 10:
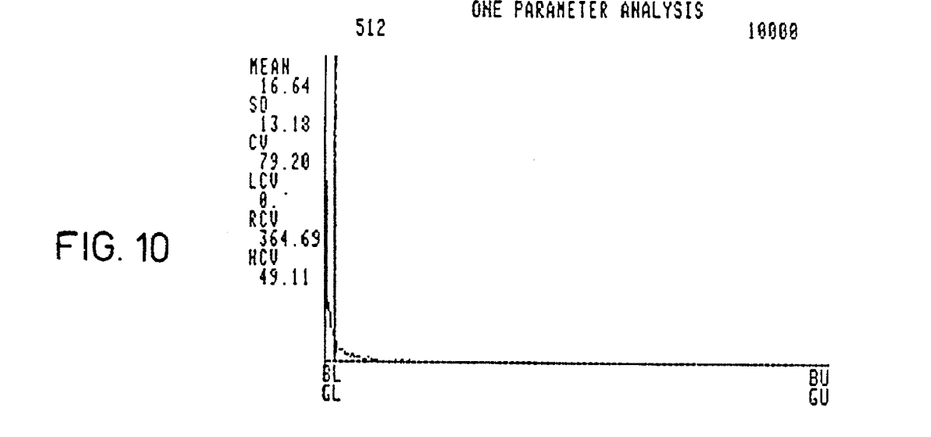
FIG. 10 shows a FACS analysis for AHT-54 and HPBL.
Figure 11:
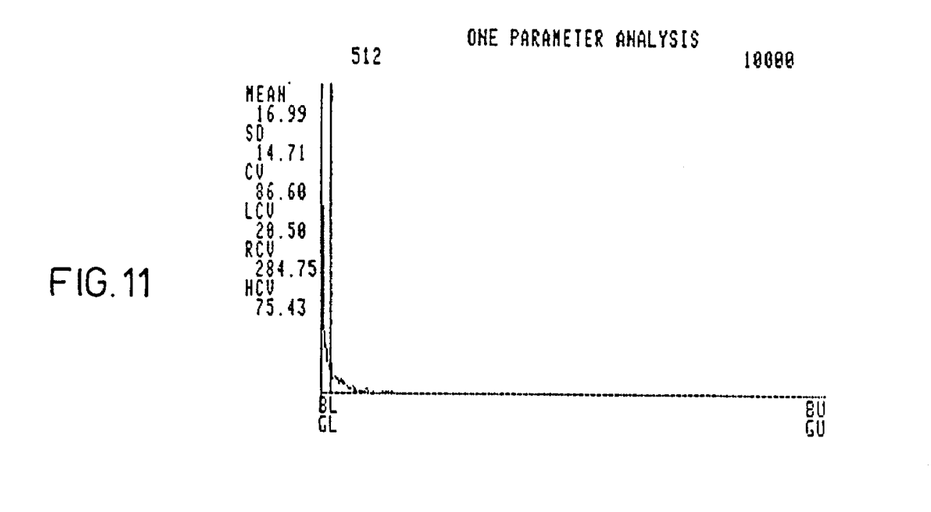
FIG. 11 shows a FACS analysis for AHT-107 and HPBL.

FIG. 6 shows the negative control. The TSH antibody did not bind to the T-lymphoblasts. In FIGS. 7 and 8 it is shown that AHT-54 (FIG. 7) and AHT-107 (FIG. 8) bind to the lymphoblasts. FIGS. 9 to 11 refer to the same experiment except that lymphoblasts are substituted by HPBL. No reaction occurs with any of the three antibodies.

It will be appreciated that the instant specification and claims are set forth by way of illustration and not limitation, and that various modifications and changes may be made without departing from the spirit and scope of the present invention.

We claim:

1. A chimeric mouse-human monoclonal antibody that specifically binds to the human interleukin-2 receptor, wherein the variable region of said antibody is identical to that of monoclonal antibody AHT-54 produced by the hybridoma deposited under accession number ECACC 86041801 and the Fc region of said antibody is obtained from a human antibody.

2. A chimeric mouse-human monoclonal antibody that specifically binds to the human interleukin-2 receptor, wherein the variable region of said antibody is identical to that of monoclonal antibody AHT-107 produced by the hybridoma deposited under accession number ECACC 86041802 and the Fc region of said antibody is obtained from a human antibody.

* * * * *